(12) United States Patent
Parenti Castelli

(10) Patent No.: US 8,075,625 B2
(45) Date of Patent: Dec. 13, 2011

(54) ORTHOPAEDIC DEVICE AND PROCEDURE TO REALIZE SUCH A DEVICE

(75) Inventor: Vincenzo Parenti Castelli, Bologna (IT)

(73) Assignee: Alma Mater Studiorum—Universita' di Bologna, Bologna (IT)

( * ) Notice: Subject to any disclaimer, the term of this patent is extended or adjusted under 35 U.S.C. 154(b) by 218 days.

(21) Appl. No.: 12/159,474

(22) PCT Filed: Dec. 28, 2006

(86) PCT No.: PCT/IB2006/003787
§ 371 (c)(1),
(2), (4) Date: Jun. 27, 2008

(87) PCT Pub. No.: WO2007/074387
PCT Pub. Date: Jul. 5, 2007

(65) Prior Publication Data
US 2008/0306604 A1 Dec. 11, 2008

(30) Foreign Application Priority Data
Dec. 28, 2005 (IT) ............................. BO2005A0795

(51) Int. Cl.
*A61F 2/38* (2006.01)
(52) U.S. Cl. ............... 623/20.21; 623/19.11; 623/20.11; 623/20.24; 623/20.28; 623/21.11
(58) Field of Classification Search .................. None
See application file for complete search history.

(56) References Cited

U.S. PATENT DOCUMENTS

| | | | |
|---|---|---|---|
| 3,932,045 A | 1/1976 | Hillberry et al. | |
| 3,945,053 A | 3/1976 | Hillberry et al. | |
| 3,969,773 A | 7/1976 | Menschik | |
| 4,267,608 A | 5/1981 | Bora, Jr. | |
| 4,865,606 A | 9/1989 | Rehder | |
| 5,405,408 A | 4/1995 | Pitkin | |
| 5,549,689 A | 8/1996 | Epstein et al. | |
| 2006/0025865 A1 | 2/2006 | Reich et al. | |

FOREIGN PATENT DOCUMENTS

| | | |
|---|---|---|
| EP | 0303195 A | 2/1989 |
| EP | 0528080 A | 2/1993 |
| FR | 2241284 A | 3/1975 |
| FR | 2290883 A | 6/1976 |
| FR | 2502937 A | 10/1982 |
| WO | WO2004069089 A | 8/2004 |
| WO | WO2004069103 A | 8/2004 |

*Primary Examiner* — David H Willse
*Assistant Examiner* — Javier Blanco
(74) *Attorney, Agent, or Firm* — Pearne & Gordon LLP

(57) ABSTRACT

An orthopaedic device (1) for the mobile connection of a first and a second bony segment (4, 5) of an organic device for cooperating with or substituting a natural articulation comprising a first working surface (9) related to the first cooperating segment (4) with a second working surface (10) related to the second bony segment (5) in order to constrain (guide) the relative motion between the said bony segments (4, 5); the first and the second working surface (9, 10) are respectively practically shaped as the axodes of the relative motion of a first and a second link of a linkage practically equivalent to the natural articulation; in particular the first and the second link are corresponding, in the linkage, to the first and the second bony segment (4, 5).

7 Claims, 6 Drawing Sheets

ORTHOPAEDIC DEVICE AND PROCEDURE TO REALIZE SUCH A DEVICE

TECHNICAL FIELD

This invention deals with an orthopaedic device and in particular with an orthopaedic device aimed at collaborating or at replacing impaired articulations.

BACKGROUND ART

The known artificial orthopaedic devices—among which are the external or prosthetic devices, the orthoses, and the internal prostheses or articular prostheses—find a wide use in the medical as well as chirurgical fields.

In the articulations (here we refer to a generic articulation although, for the sake of clarity we will refer to the knee articulation) there are surfaces, so called articular surfaces, that come to contact with each other and have a relative motion of rolling and sliding, and together define a desired relative motion.

This relative motion is guaranteed by articular structures such as ligaments, muscles and cartilaginous structures whose aim is, in particular, to maintain the relative position of the articular surfaces.

When the articular surfaces are impaired because of various pathologies or injuries or are missing because of traumatic or chirurgical amputations, their functionality may be restored by resorting to internal or external prostheses while, when the natural articulation is still existing but with a limited functionality, orthopaedic tutors are used to help or restore the impaired or compromised functions.

Internal prostheses try to replicate the impaired natural articular surfaces by substituting them by cams and other intermediate elements (for instance menisci of plastic material) which replicate the natural movement of the natural articulation.

In particular, the original movements is partly replicated by relying upon the shape of the conjugated surfaces of the prosthesis, which are manufactured with a shape similar to that of the original surfaces, and partially by relying on the natural articular structures not sacrificed during the surgical intervention necessary to implant the prosthesis.

It should be noticed that during the implantation of an internal prosthesis, the most important articular structures, such as for instance the cruciate ligaments in the knee prosthesis, are frequently removed in order to allow the insertion of the prosthesis and consequently the optimal conditions for maintaining the relative position of articular surfaces are destroyed.

The conjugate surfaces that come to contact with each other during the motion have a strong relative sliding motion which causes high wear due to friction and high loads per unit of surface.

In order to reduce the negative effects of the sliding, an intermediate element with a low friction coefficient is often introduced between the articular surfaces.

The external prostheses, used to completely substitute the articulation, are generally complex mechanisms which try to replicate at the best the relative motion of the substituted articulation and are therefore mechanically complex and expensive.

Similarly the existing orthoses guide the relative motion of the main elements of the natural articulation only approximately and are relatively complex.

Summarizing, the known orthopaedic devices are capable to replicate the natural motion only approximately, have elements which exhibit a high sliding relative motion with consequent strong wear which reduces their life, are mechanically complex and are expensive.

Moreover, in general it is very difficult to maintain the correct relative position between the conjugate surfaces which are in contact with each other, therefore (especially for internal prostheses) their relative motion can be hardly controlled.

DISCLOSURE OF THE INVENTION

In this context, the main technical aim of the present invention is to propose an orthopaedic device which is free from the above said drawbacks.

One target of the proposed invention is to present an orthopaedic device which in practice eliminates the friction between the moving parts.

A further target of the present invention is to propose an orthopaedics device which better replicates the functionality of the replaced or supported articulation.

A further target is also the realization of an orthopaedic device whose articulated parts are firmly and precisely maintained in the relative optimal position for their correct functioning.

Another target of the present invention is the realization of an orthopaedic device suitable to bear the forces normally and exceptionally applied to the replaced articulation.

BRIEF DESCRIPTION OF THE DRAWINGS

Further characteristics and advantages of the present invention will be more clear from the exemplificative description, and therefore not limitative, of a shape of preferred but not exclusive realization of an orthopaedic device as shown in the pictures, where.

DETAILED DESCRIPTION OF THE PREFERRED EMBODIMENTS OF THE INVENTION

According to the annex drawings, by the number 1 an orthopaedic device is shown according to the present invention.

Figure 1:
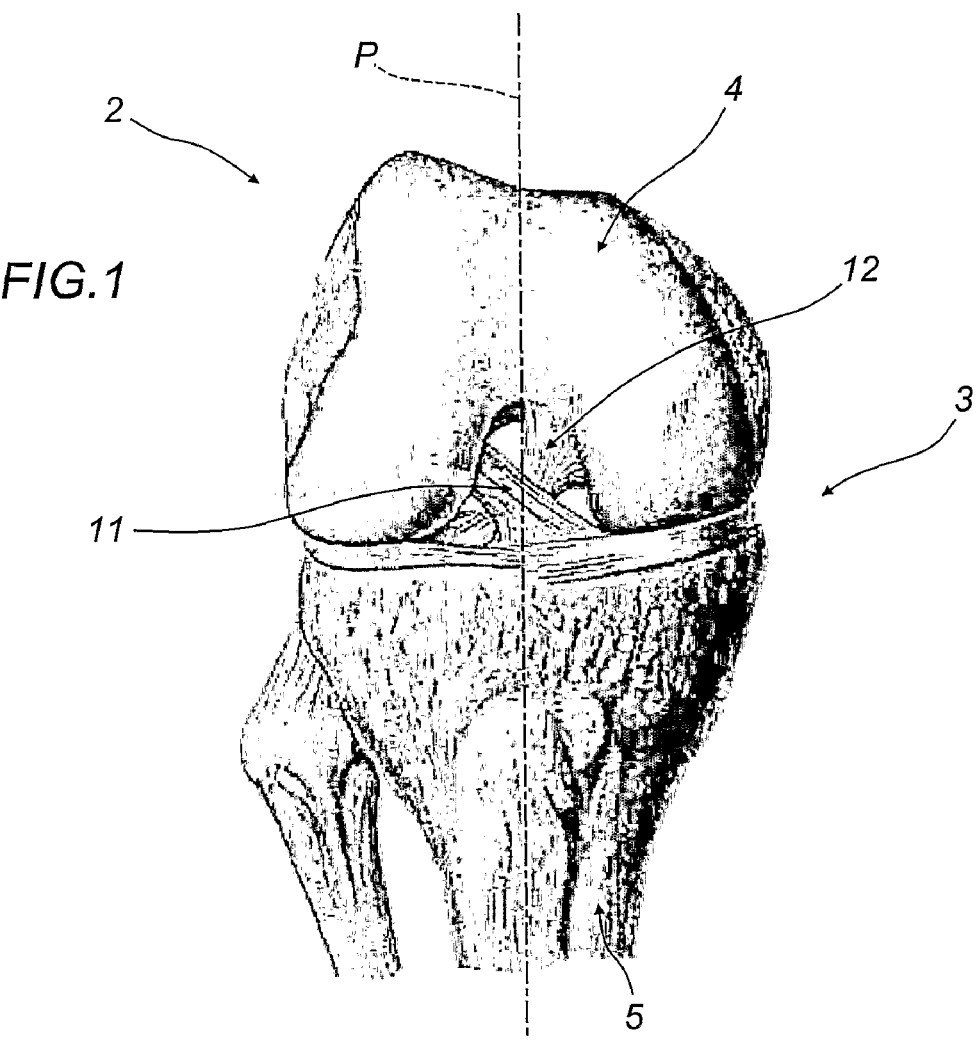
FIG. 1 shows a natural articulation, with some parts removed, in a schematic frontal view.

According to what is shown in FIG. 1, the orthopaedic device 1 is for supporting or replacing, at least partially, a natural articulation 2.

As an example, without loosing generality, according to what is shown in FIG. 1, we refer in the following, for more clarity, to a knee 3 in the sense of natural articulation 2 between femur 4 and tibia 5 where femur 4 and tibia 5 mean a first and a second bony segment 4, 5.

In the following, as an example and without losing generality, we refer to, for more clarity, an orthopaedic device 1 for internal prostheses.

The orthopaedic device 1 and the procedure for its construction according to the present invention can be conveniently applied also for external prostheses and orthoses for knees, ankles, elbows, and shoulders, although the description of these is not reported in detail since it is conceptually similar to that reported previously as an example for an internal knee prosthesis.

The device 1 comprises a first structural element 6 associated, in a substantially known way, to the femur 4 and a second structural element 7 associated, in a substantially known way, to the tibia 5.

The elements 6 and 7 are maintained in a relative working position by means of suitable connecting elements 8 which will be better described in the following.

The element 6 exhibits a proper working surface 9 defined, as it will be explained in what follows, as a portion of a first ruled surface with a curvilinear directrix, that is, as a portion of a surface generated as envelope by a straight line (generatrix) along a curve (directrix).

The second element 7 exhibits a proper working surface 10 defined, as it will be clarified in the following, as a portion of a second ruled surface with a curvilinear directrix.

The surfaces 9 and 10 cooperate to guide the relative motion of the femur 4 and the tibia 5 by means of the above mentioned connecting elements 8.

In particular, as it will be better described in the following, the surfaces 9 and 10 roll one over the other one without sliding.

The surfaces 9 and 10 are in particular shaped, substantially, apart from the connecting elements 8, as axodes or primitive surfaces of the relative motion of the bony segments 4, 5.

Figure 2:
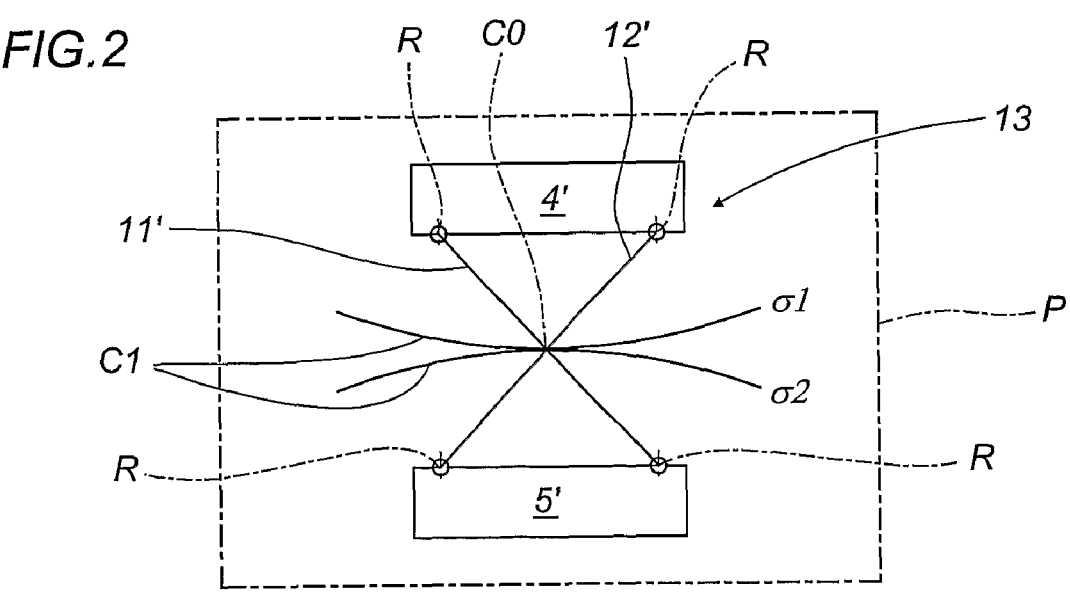
FIG. 2 shows in a schematic frontal view a linkage which is practically equivalent to the main articular structures of the natural articulation of FIG. 1 viewed from the left side.

According to what is shown in the FIGS. 1 and 2, the knee 3 that is the articulation 2 taken as an example, schematically comprises the femur 4, the tibia 5, a first ligament 11, known as anterior cruciate ligament, and a second ligament 12, known as posterior cruciate ligament.

The motion of the knee 3 as schematically described can be assimilated to, in a substantially know way, either a planar rigid motion, or to a motion of a body whose points have velocities that are always parallel to a plane P, in particular to a plane P substantially perpendicular to the plane of FIG. 1.

In other words, the motion of the knee 3 is assimilated to a motion for which all points have trajectories which are contained in planes parallel to the reference plane P, that is the plane of motion.

For this reason, in a known manner, the knee 3 can be assimilated to a planar linkage lying on the plane P whose parts will be labelled by hyphened reference numbers equal to the reference number which indicate the corresponding parts of the knee 3.

It is important to note that a substantially analogous study can be done for whatever articulation 2.

According to what is shown in the FIG. 2, the reference planar linkage is a for-bar linkage 13, being known in particular that the ligaments 11 and 12, formed as it is known by fibres, comprises a fibre which does not change its length during motion, that is there are points of insertions of the ligaments 11 and 12 on the bony segments 4, 5 which during motion maintain a mutual constant distance, that is to say that the above said fibre is practically isometric.

The four bar linkage 13 comprises a first link or rigid body 4', a second link or rigid body 5', a third link 11' and a forth link 12' each other interconnected by means of elementary kinematic pairs with one degree of freedom, in particular by joints with revolute axis R perpendicular to the plane of FIG. 2 which coincides with the above cited plane P.

It should be noticed that in the shown particular case of planar motion, the cited first and second ruled surface with curvilinear directrix are, as it will be seen, cylindrical surfaces or surfaces for which the generatrix line moves on the directrix while remaining parallel to itself.

We will refer to, in particular as an example, a rigid planar motion but the concept can be extended to a rigid spherical motion and, by suitable approximations, also to a general spatial motion, as it will be shown with more detail in what follows.

With reference to FIG. 2, the relative planar motion of the two rigid bodies 4' and 5' in the plane of the figure can be always be described as a succession of rotational instantaneous motions, that is at each instant we can think of a relative infinitesimal motion of the two rigid bodies about one point.

Collecting the points about which the bodies 4' and 5' instant by instant rotate about (locus of the centers of instantaneous rotation) we obtain, for an observer fixed to the rigid body 4', a curve σ1 and for an observer 2 fixed to the rigid body 5', a curve σ2 (the curves σ1 and σ2 are known as centroids of the relative motion).

The two curves σ1 and σ2 at any instant roll one with respect to the other about a point which is the instantaneous centre of rotation (C0 in the shown configuration) and in a successive instant they come to contact in another point C1 which becomes the centre of instantaneous rotation at the instant successive to the rotation about point C0).

The relative motion of the two bodies 4' and 5' occur while the two curves σ1 and σ2 are rolling one on the other without sliding.

In the orthopaedic device 1 the above cited surfaces 9 and 10 are defined as the ruled surfaces that have as directrices the curves σ1 and σ2 respectively; such ruled surfaces with curvilinear directrix are, as already mentioned, cylindrical surfaces having considered the motion as a planar motion.

The surfaces 9 and 10 considered in the plane of motion have, substantially apart of the connecting elements 8, the shape of the curves σ1 and σ2.

The orthopaedic device 1 therefore allows the bony segment 4 and the bony segment 5 to replicate, substantially, the relative motion of links 4' and 5' of the four-bar linkage 13 which is basically equivalent to the articulation 2.

In other words, in the orthopaedic device 1, a physical meaning is given to the curve σ1, which generates the working surface 9, and to the curve σ2 which generates the working surface 10.

In the preferred physical shape shown as an example, the elements 8 are suitably shaped in order to allow the rotation, substantially pure, of the surfaces 9 and 10.

The connecting elements 8 comprise a series of flexible elements 14, 15, and 16, preferably of laminar type.

Such elements 14, 15, 16 are constrained to the working surfaces 9, 10.

In particular, the element 14 is fixed, in a substantially correspondence with its own first extremity 14a, in one extremity portion A of the element 7.

Moreover, the element 14 is fixed, in a substantially correspondence with its own second extremity 14a, in one extremity portion B of the element 6.

The element 14 partially wraps itself around the surface 10, substantially from the portion A until one axis of instantaneous rotation.

Figure 4:
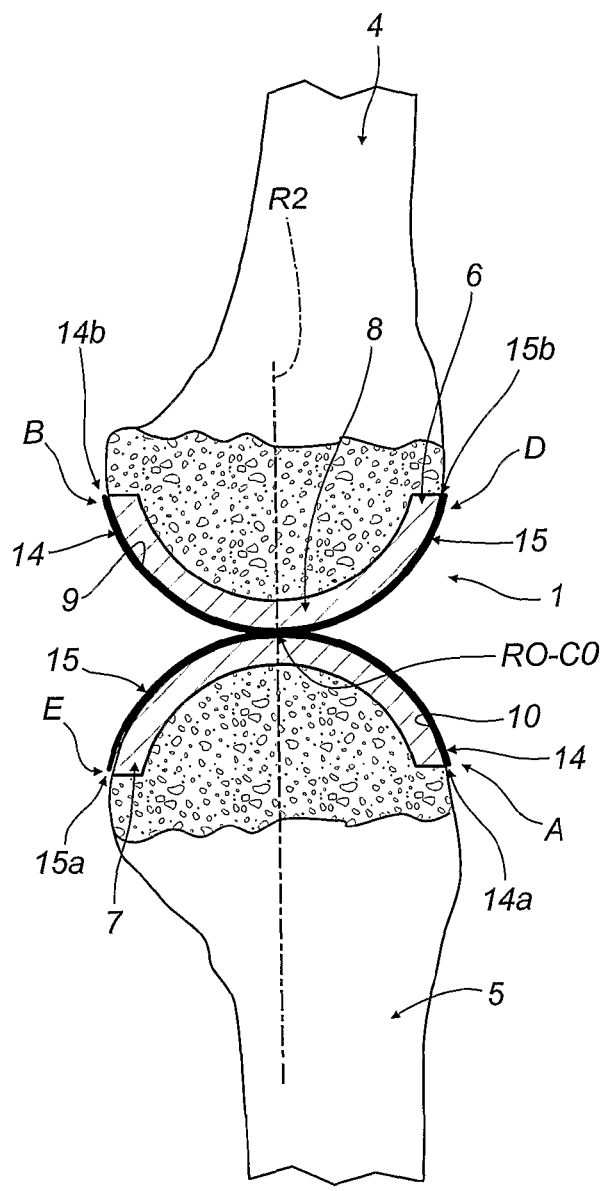
FIG. 4 shows, in a suitable section of the schematic lateral view, the orthopaedic device of FIG. 3 in a first working configuration where some parts are removed for clarity.
Figure 5:
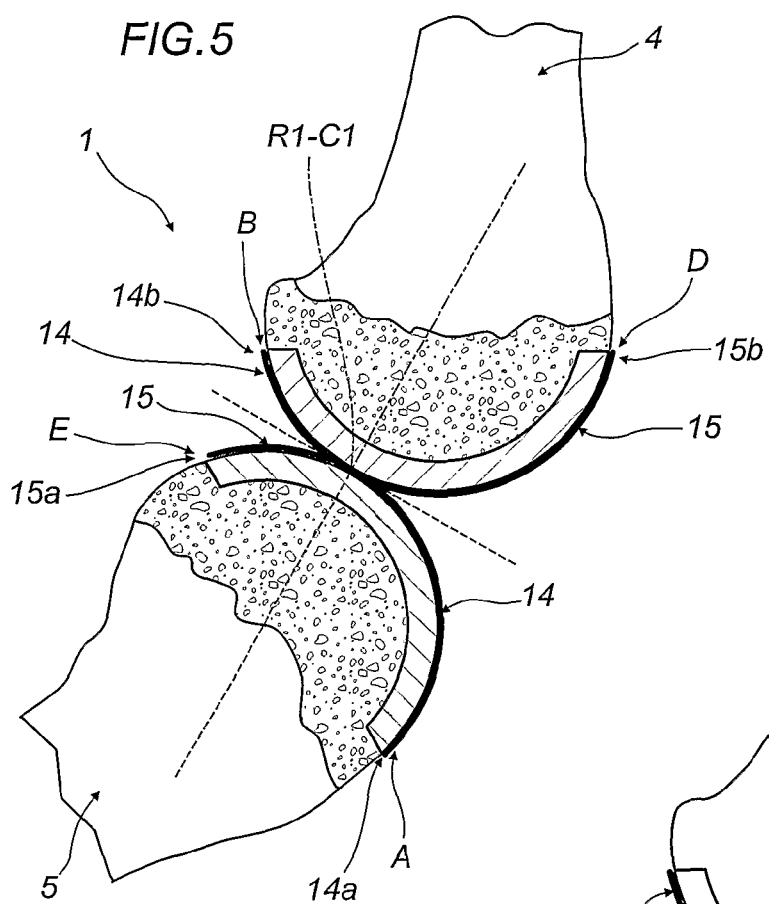
FIG. 5 shows, in a suitable section of the schematic lateral view, the orthopaedic device of FIG. 3 in a second working configuration where some parts are removed for clarity.
Figure 6:
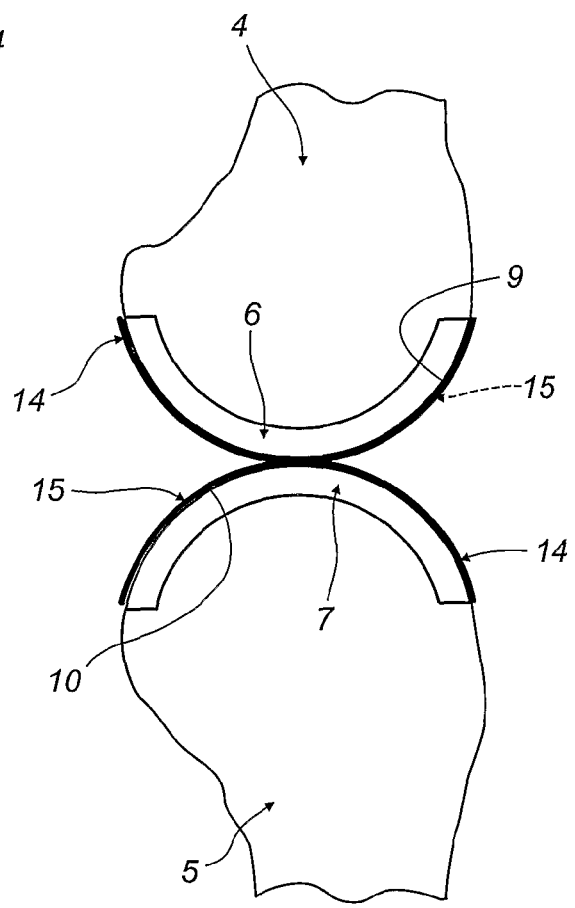
FIG. 6 shows, in a schematic lateral view, the orthopaedic device of FIG. 3 where some parts are removed for clarity.

With particular reference to FIGS. 4 and 5, considering the motion as planar, by the reference points C0 and C1 are indicated the instantaneous centres of rotation in a first and in a second operating configuration, that is in two successive instants of time, in the relative motion of the bony segment 5 with respect to the bony segment 4 through the orthopaedic device 1.

Axes R0 and R1 of instantaneous rotation correspond to the centres of instantaneous rotation C0 and C1 and are coincident, substantially, with a generatix of the surfaces 9 and 10 at the two considered instants of time.

Such axes of instantaneous rotation R0 and R1 coincide with the generatrix of common contact to the two surfaces 9 and 10, at the considered instants.

The element 14 partially wraps itself around the surface 9, substantially from the instantaneous axis of rotation R0, R1 until the portion B.

Practically the element 14 is fixed to the extremities 14a, 14b, respectively to the surfaces 9 and 10.

As long as the bony segment 5 moves from the said first and second operative configuration, the flexible element 14 unwraps itself from the surface 9 and wraps itself around the surface 10.

As long as the bony segment 5 moves from the said second and said first operative configuration, the flexible element 14 unwraps itself from the surface 10 and wraps itself about the surface 9.

The element 15 is fixed in a substantially equivalent correspondence with one of its own extremities 15a, in one portion E of the extremity of the element 7.

Moreover, the element 15 is fixed in a substantially equivalent correspondence with its second extremity 15b, in one portion D of the extremity of the element 6.

The element 15 wraps itself in part about the surface 10, substantially from the portion E until the axes R0, R1.

The element 15 wraps itself in part about the surface 9, substantially from the instantaneous axis of rotation R0, R1 until to the portion D.

In practice the element 15 is fixed to the extremities 15a, 15b respectively to the surfaces 10 and 9.

As long as the bony segment 5 moves from the said first to the said second operative configuration, the flexible element 15 unwraps itself from the surface 10 and wraps itself about the surface 9.

As long as the bony segment 5 moves from the said second to the first operative configuration, the flexible element 15 unwraps itself from the surface 9 and wraps itself about the surface 10.

It should be noticed that, preferably, the flexible element 15 is wrapped about the working surfaces 9, 10 with a symmetric way with respect to the flexible element 14.

The flexible element 16 is located symmetrically, together with the flexible element 14, with respect to the flexible element 15.

In particular the element 16 is fixed, in a substantially correspondence with one of its own extremity 16a in the extremity portion A of the element 7.

The element 16 is also fixed, in a substantially correspondence with its own second extremity 16b in the extremity portion B of the element 6.

The element 16 wraps itself in part about the surface 10, substantially from the portion A until the axis R0 or R1 of instantaneous rotation.

The element 16 wraps itself in part about the surface 9, substantially from the axis R0 or R1 of instantaneous rotation until the portion B.

In practice the element 16 is fixed through its extremities 16a, 16b respectively to the surfaces 10 and 9.

As long as the bony segment 5 moves from the said first to the second operative configuration, the flexible element 16 unwraps itself from the surface 9 and wraps itself about the surface 10.

As long as the bony segment 5 moves from the said second to the first operative configuration, the flexible element 16 unwraps itself from the surface 10 and wraps itself about the surface 9.

The elements 14, 15, and 16 in the way they are located allow the surfaces 9 and 10 to roll one on the other one without sliding.

Figure 3:
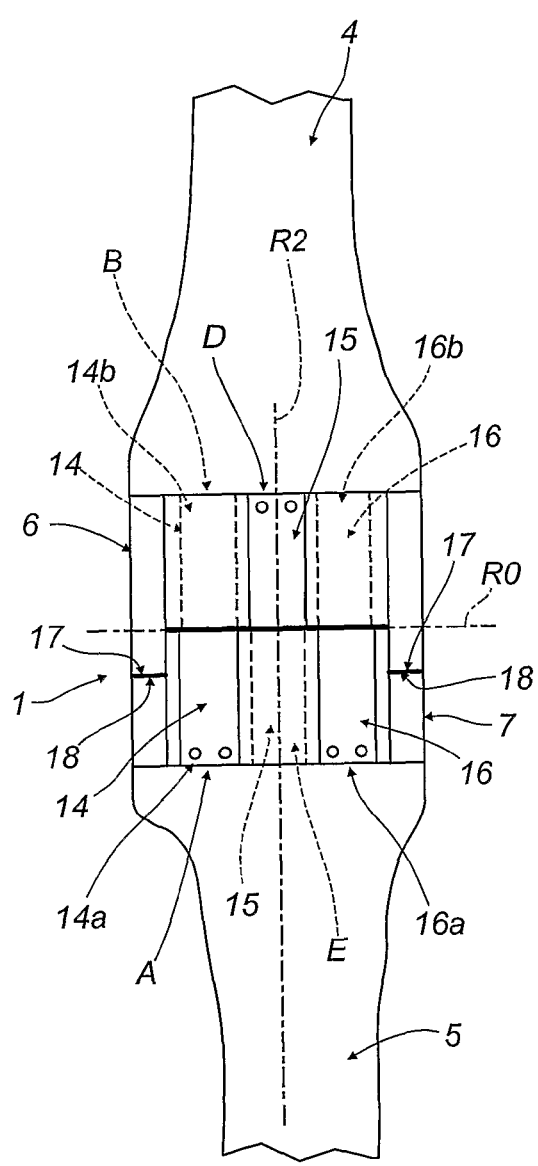
FIG. 3 shows a first practically feasible shape of an orthopaedic device according to the present invention in a schematic frontal view.

With particular reference to the FIGS. 3 and 4, it can be noted that the elements 14, 15 and 16 in the way they are located prevent the bony segments 4, 5 to roll one with respect to the other about a axis R2 substantially perpendicular to the surfaces 9 and 10.

In other words, whatever of the elements 14, 15 or 16 prevents that the other two become slack or leave the contact with the surfaces 9 and 10.

It should be noticed that the working surfaces 9 and 10 devoted to roll one on the other one without sliding and obtained from the said curves σ1 and σ2 are also suitably sized, as said, for taking into account the thickness, different from zero, of the flexible elements 14, 15 and 16.

Figure 7:
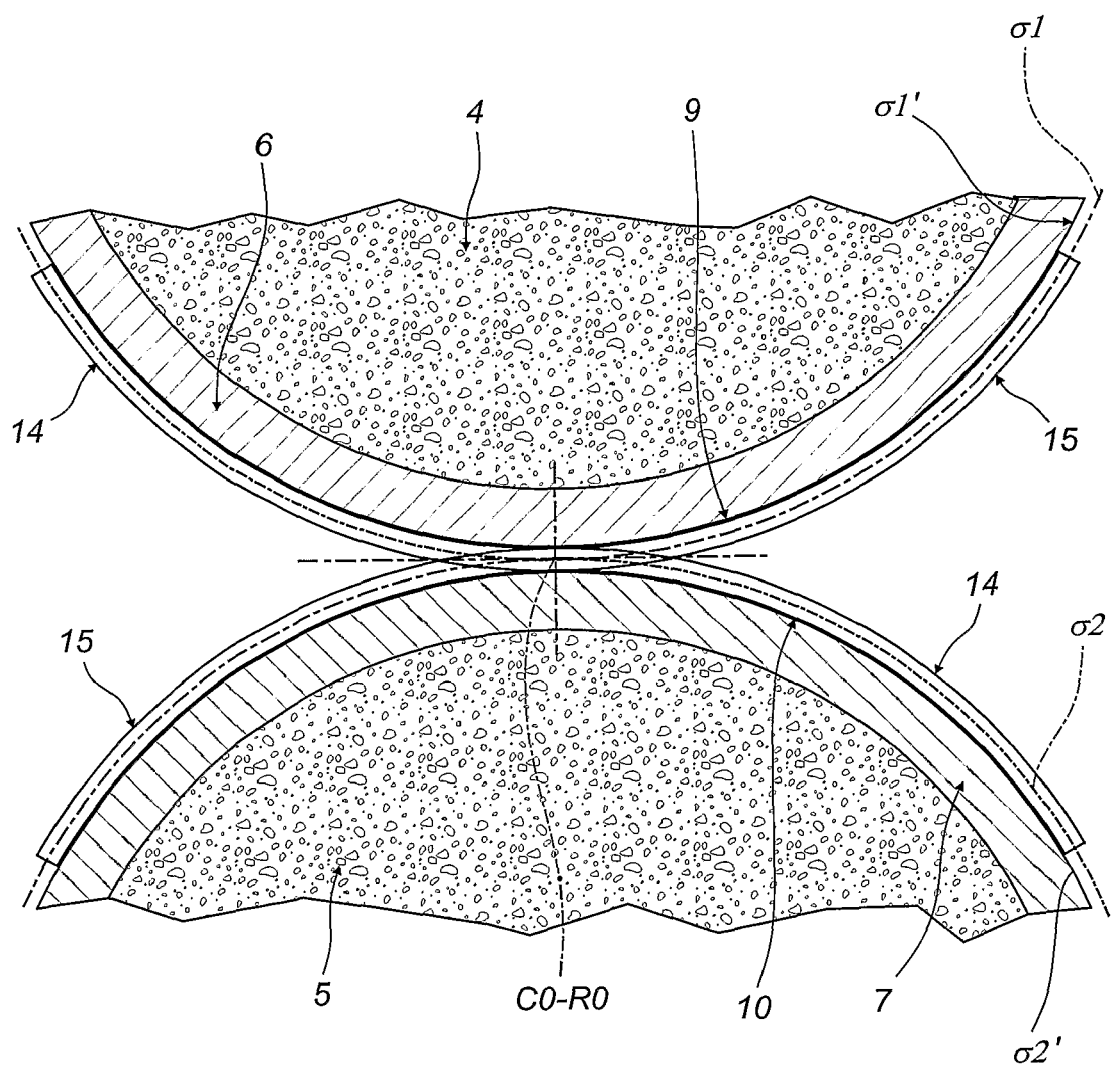
FIG. 7 shows, in a schematic lateral view, an enlarged particular of the orthopaedic device according to the present invention.

According to what shown in the FIG. 7 as an example, in the preferred physical shape shown, the transverse sections of the working surfaces 9, 10 have substantially as curvatures the curves σ1' and σ2' in such a way that the centre C of instantaneous rotation be instant by instant in the crossing point of the flexible elements 14, 15 and 16.

The centre C superimposes with the contact point of the said curves σ1 and σ2 so as the relative motion of the bony segments 4, 5 is substantially of pure rolling.

For the sake of clarity of exposition the working surfaces 9, 10 are however considered as the axodes of motion, that is as the sections of the surfaces 9, 10 on the plane of motion overlap practically with the curves σ1 and σ2.

The obtained device 1 allows the bony segments 4, 5 to replicate the relative motion that is performed in the natural articulation 2.

The working surfaces 9, 10 substantially roll one on the other eliminating practically the sliding among them, thus reducing friction and wear, increasing the life of the prosthesis and increasing its reliability.

It is worth noting that the connecting elements 8 work primarily in traction and the flexible elements 14, 15, and 16 are loaded in the optimal way.

Figure 9:
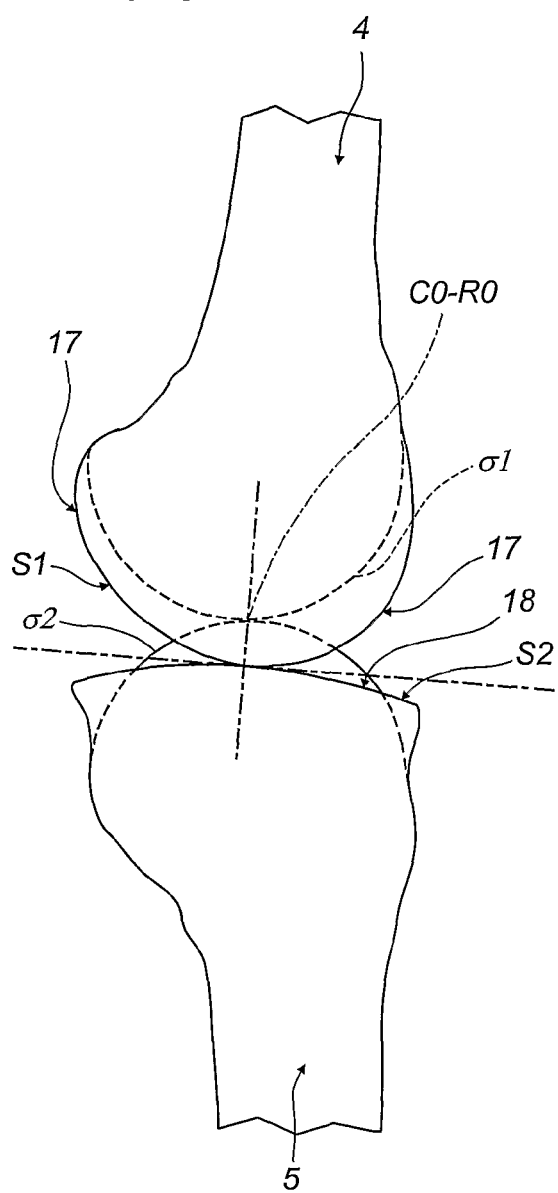
FIG. 9 shows the orthopaedic device of FIG. 3 in the first working configuration, in a schematic lateral view, where some parts are removed for clarity.
Figure 10:
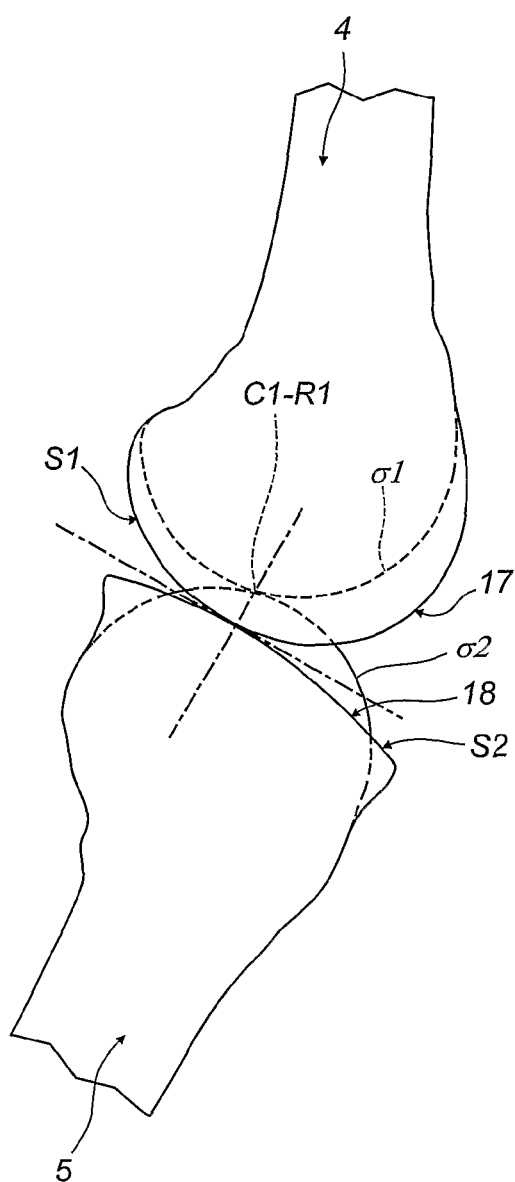
FIG. 10 shows the orthopaedic device of FIG. 3 in the second working configuration, in a schematic lateral view, where some parts are removed for clarity.

According to what is shown in FIGS. 3, 9 and 10 the first structural element 6 presents a portion of its own surface in front of the second structural element 7, defined as loading surface 17, having profile S1.

The second structural element 7 presents a portion of its own surface in front of the first structural element 6, defined as loading surface 18, having profile S2.

The loading surfaces 17, 18 are conjugate surfaces, as it will be clarified in what follows.

The loading surfaces 17, 18 are preferably realized starting from the centrodes σ1 and σ2 of the surfaces 9, 10 and from a pair of conjugate profiles S1 and S2 associated with the centrodes σ1 and σ2.

Moreover, according to what is shown in FIG. 3, the structural element 6 comprises, preferably, a pair of loading surfaces 17 located symmetrically with respect to the flexible element 15 and, for each surface 17, a correspondent conjugate loading surface 18. We will refer in the following, for the sake of clarity, to a pair of conjugate surfaces 17, 18.

In particular, the conjugate profiles S1 and S2 are realized, in a substantially known way, as conjugate profiles which are always in mutual contact one with the other during the rolling motion of the corresponding primitives (centrodes), that is of the centrodes σ1 and σ2.

The conjugate profiles S1 and S2 are designed, in a known way which is not described in detail, in such a way to be prevalently orthogonal to the forces transmitted among the first and the second bony segment.

Preferably, the profiles S1 and S2 are obtained by considering the curves σ1 and σ2 as their respective primitives (centrodes) of motion and are preferably determined as a function of the linkage 13.

Such a loading conjugate surfaces 17, 18 are devoted to the transmission of the forces between the bony segments 4, 5 while, as said before, the working surfaces 9, 10 are devoted, basically, to guide the relative motion of the bony segments 4, 5.

Figure 8:
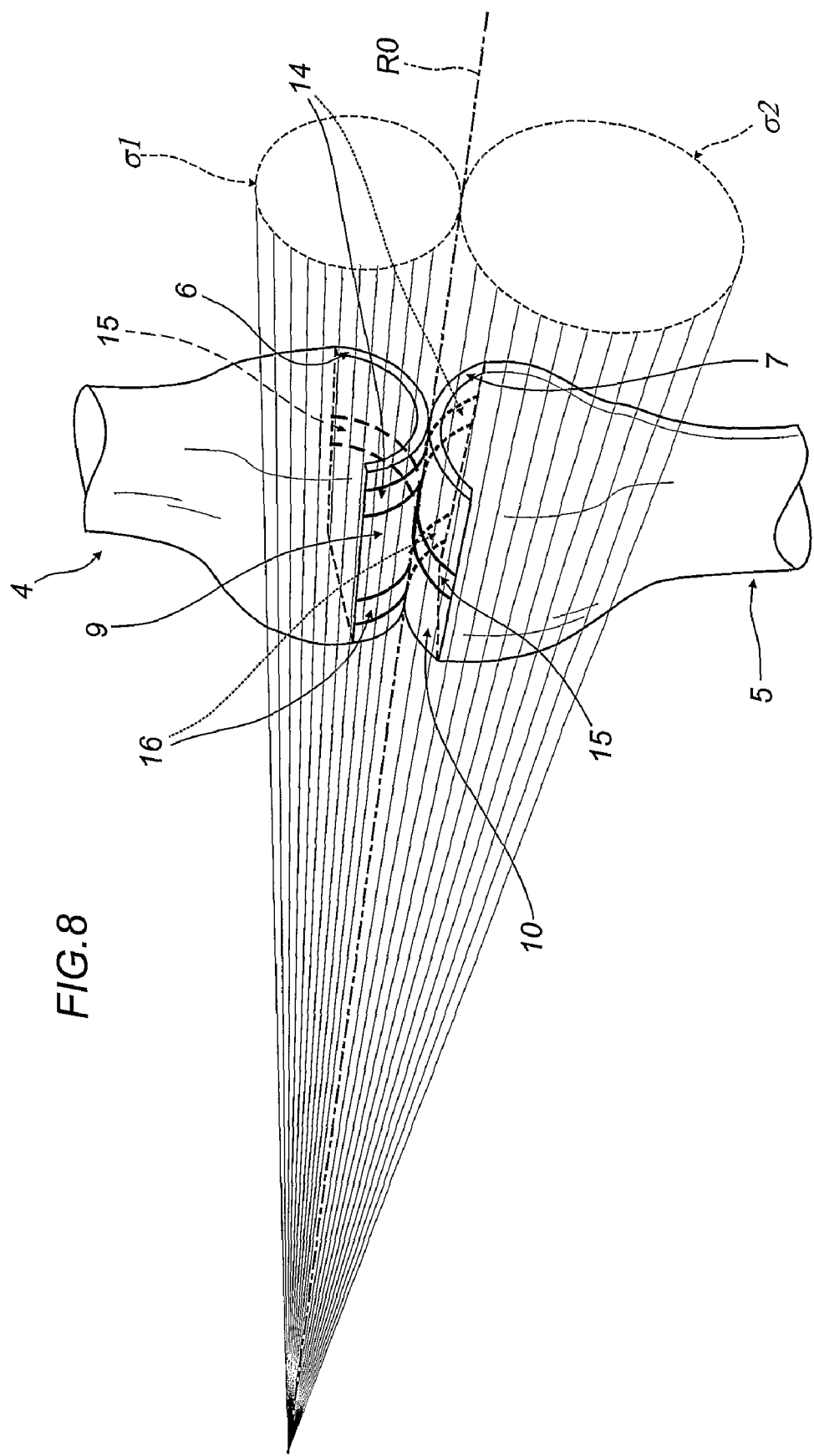
FIG. 8 shows a second practically feasible shape of the orthopaedic device according to the present invention in a schematic perspective.

With particular reference to FIG. 8, in the shown preferred physical shape, the device 1 is realized having approximated, in a substantially known way, the motion of the articulation 2 to a spherical motion, that is to say that the motion of the articulation 2, in particular for the knee 3, is assimilated to a succession of instantaneous rotations about an axis passing through a fixed point.

More precisely, the articulation 2 is approximated with a spatial linkage not shown in which the links corresponding to the cited first and second bony segments 4, 5 move with a spherical motion.

The axis of instantaneous rotation, still passing through the fixed point, changes its orientation according to the relative motion between the links, and the geometrical locus of the positions it occupies during the motion is a first conic surface for the first link and a second conic surface for the second link.

The motion of the articulation 2 is completely defined by the rolling on the first conic surface of the second conic surface.

In practice the first and second cited ruled surfaces with a curvilinear directrix, and then the said first and second working surfaces 9, 10, are conic surfaces in the sense of surfaces for which the generatrix line moves on the directrix and passes through a fixed point.

It is important to observe that in the spherical motion the directrices are still curves which for the sake of simplicity can be still indicated with σ1 and σ2.

The conic surfaces, axodes of the spherical motion, have in common the vertex and they touch each other along a generatrix which coincides with the axis of instantaneous rotation at the instant considered.

Therefore, by considering the spherical motion, analogously to the case of planar motion, the first and second element 6, 7 present respective working surfaces 9, 10 defined, substantially, by the axodes of motion.

The orthopaedic device 1, in which the surfaces 6, 7 are defined as portions of a respective ruled surface with curvilinear directrix in which all the lines pass through a fixed point, presents one degree of freedom as in the case of cylindrical ruled surfaces and also in the case in which the motion of the articulation 2 is approximated to a planar motion.

It is worth observing that the general idea of the centrodes (axodes) can be deduced, as described, starting from the planar or spatial four-bar linkage taken as equivalent mechanism, but it can more generally be deduced from the axodes of the real natural motion, that is from the relative motion experimentally measured.

In particular, the natural motion being a spatial one, σ1 and σ2 represent the directrices of the axodes in case of planar motion or the (spherical) directrices on of the sphere of motion in case of spherical motion, or the directrices as above defined of the axodes of a planar or a spherical motion which represent an approximation of the real spatial motion which instantaneously is a helicoidal motion.

For the sake of simplicity, we referred to equivalent mechanisms which represent a first good approximation of the motion of the considered articulation.

The procedure for the realization of the orthopaedic device 1 implies to study the natural articulation 2 to be supported or replaced with a linkage 13, for instance planar or spherical, substantially equivalent to the articulation 2 itself.

From the equivalent linkage 13 both the centrodes σ1 and σ2 of the relative motion of the two rigid bodies 4', 5', can be obtained, these last ones being corresponding to the bony segments 4, 5 of the reference articulation 2, and the motion of the articulation 2 approximated to a planar or to a spherical motion can also be obtained.

For the sake of simplicity one of the two rigid bodies 4', 5' is taken as the fixed frame.

Alternatively, as above said, the natural articulation 2 is experimentally studied and the axodes of the real motion are obtained As it is well known, these surfaces roll and slide one over the other: neglecting, for instance, the sliding component, from these axodes the centrodes of the relative motion, that is the directrices (as defined above) of the axodes of a planar or of a spherical motion which represent an approximation of the real spatial motion, can be found.

Once the centrodes of motion have been found a physical meaning can be given to them.

In the case of planar motion the transverse section of the surface 9 of the element 6 associated with the bony segment 4 is shaped as the centrode σ1 of the motion corresponding to the rigid body 4' of the four-bar linkage 13.

In the case of planar motion the transverse section of the surface 10 of the element 7 associated with the bony segment 5 is shaped as the centrode σ2 of the motion corresponding to the rigid body 5' of the four-bar linkage 13.

In general the surfaces 9 and 10 are built as portions of the ruled surfaces with a curvilinear directrix where the directrices are respectively the centrodes σ1 and σ2.

As said above, the ruled surfaces are cylindrical in the case of planar motion or conic in case of spherical motion.

The elements 6 and 7 are reciprocally constrained and guided by the connecting elements 8 which allow the working surfaces 9, 10 to roll one over the other one without sliding.

The third and forth loading surfaces 17, 18, each to the other conjugated, defined starting from the profiles S1 and S2 conjugated in the plane or on the sphere of motion, are also preferably and respectively associated to the working surfaces 9, 10.

In the preferred physical shape the conjugate loading surfaces 17, 18 are practically the anatomical surfaces of the bony segments 4, 5, or an artificial replica of them, which are however guided, as above mentioned several times, by the working surfaces 9, 10 and by the connecting elements 8.

Such a solution has particular advantages with respect to the known prostheses since in these the relative motion between the elements that come to contact is not suitably guided because, quite often, the principal ligaments are cut and not replaced with adequate connecting elements.

The device 1 makes it possible to precisely guide the relative motion between the interconnected bony segments.

The axodes of motion that roll one on the other do not exhibit any sliding behaviour.

The invention as it is conceived is susceptible of evident industrial applications; moreover, it can be object of numerous modifications and variation all comprised in the inventive concept. Moreover, all details may be substituted by equivalent technical elements.

The invention claimed is:

1. Orthopaedic device for the mobile connection of a first and a second bony segment of an organic apparatus for substituting or cooperating with a natural articulation, said device comprising a first articulating surface associated to said first bony segment and a second articulating surface associated with said second bony segment, said first and second articulating surfaces collaborating in order to guide the relative motion between said bony segments, said first and second articulating surfaces being configured to roll one over the other one without sliding, said first and second articulating surfaces being respectively defined as portions of a first and a second ruled surface having as directrices the centrodes of the relative motion between the first bony segment and the second bony segment, the orthopaedic device also comprising a first loading surface, having a first profile, associated to said first bony segment and a second loading surface, having a second profile, associated to said second bony segment, said first and second loading surface being devoted to the transmission of forces between said first bony segment and said second bony segment, said first and said second loading surfaces being conjugate surfaces defined as a function of the first and the second conjugate profile and the centrodes, the first and the second conjugate profile being orthogonal to the forces transmitted among the first bony segment and the second bony segment; the orthopaedic device comprising connecting elements between said first articulating surface and said second articulating surface defined by a first and a second flexible element, said first flexible element being fixed at one end to said second bony segment, and fixed at an opposite end to said first bony segment, said second flexible element being fixed at one end to said second bony segment and fixed at an opposite end to said first bony segment, wherein said first flexible element in part wraps itself about said first articulating surface and in part about said second articulating surface, said second flexible element in part wraps itself about said first articulating surface and in part about said second articulating surface, and wherein said connecting elements further comprise a third flexible element symmetrically located between said first and said second flexible elements, said third flexible element being fixed at one end to said second bony segment, and fixed at an opposite end to said first bony segment, wherein the said first and second ruled surface have as directrices the centrodes of the relative motion of a first link and a second link of a linkage equivalent to said natural articulation, said first and second links corresponding in said linkage to said first and second bony segments, wherein said relative motion is a planar or spherical motion which represents an approximation of the real spatial motion of said natural articulation.

2. Device according to claim 1, wherein said first and second ruled surfaces are cylindrical surfaces, said linkage being a planar linkage.

3. Device according to claim 1, wherein said first and second ruled surfaces are conic surfaces, said linkage being a spatial linkage for which said first and second links move according to a spherical motion.

4. Device according to claim 1, wherein the said first and second bony segments are defined respectively, in a knee, by the femur and the tibia.

5. Device according to claim 1, wherein the device defines an internal prosthesis for the said natural articulation.

6. Device according to claim 1, wherein the device defines an external prosthesis for the said natural articulation.

7. Device according to claim 1, wherein the device defines an orthosis for the said natural articulation.

* * * * *